United States Patent
Hammerland, III et al.

(10) Patent No.: US 9,833,233 B2
(45) Date of Patent: Dec. 5, 2017

(54) METHODS AND DEVICES FOR TISSUE SUTURING

(71) Applicant: Covidien LP, Mansfield, MA (US)

(72) Inventors: John Hammerland, III, Boulder, CO (US); Eric Kramer, Boulder, CO (US); Adam Carahalios, Morrison, CO (US); Todd Scott, Fort Mill, SC (US)

(73) Assignee: Covidien LP, Mansfield, MA (US)

( * ) Notice: Subject to any disclaimer, the term of this patent is extended or adjusted under 35 U.S.C. 154(b) by 323 days.

(21) Appl. No.: 14/811,976

(22) Filed: Jul. 29, 2015

(65) Prior Publication Data

US 2016/0089150 A1    Mar. 31, 2016

Related U.S. Application Data

(60) Provisional application No. 62/057,394, filed on Sep. 30, 2014, provisional application No. 62/057,387, filed on Sep. 30, 2014.

(51) Int. Cl.
*A61B 17/04* (2006.01)
*A61B 17/11* (2006.01)

(52) U.S. Cl.
CPC ...... *A61B 17/0469* (2013.01); *A61B 17/0401* (2013.01); *A61B 17/0482* (2013.01); *A61B 17/11* (2013.01); *A61B 2017/0409* (2013.01); *A61B 2017/0414* (2013.01); *A61B 2017/0459* (2013.01); *A61B 2017/0464* (2013.01); *A61B 2017/1107* (2013.01); *A61B 2017/1135* (2013.01)

(58) Field of Classification Search
CPC ............... A61B 17/11; A61B 17/0401; A61B 2017/1135; A61B 2017/1107; A61B 2017/0409; A61B 2017/0414; A61B 2017/0459; A61B 2017/0464; A61B 17/0469; A61B 17/0482
See application file for complete search history.

(56) References Cited

U.S. PATENT DOCUMENTS

| | | | |
|---|---|---|---|
| 5,037,433 A | 8/1991 | Wilk et al. | |
| 5,354,271 A | 10/1994 | Voda | |
| 5,373,840 A | 12/1994 | Knighton | |
| 5,411,520 A | 5/1995 | Nash et al. | |
| 5,480,406 A | 1/1996 | Nolan et al. | |
| 5,759,188 A | 6/1998 | Yoon | |
| 5,797,927 A | 8/1998 | Yoon | |
| 5,957,937 A | 9/1999 | Yoon | |

(Continued)

FOREIGN PATENT DOCUMENTS

EP    1607046 A1    12/2005

*Primary Examiner* — Richard Louis

(57) ABSTRACT

A suturing device is disclosed. The suturing device includes an end effector assembly disposed on a distal end of the suturing device. The end effector assembly includes at least one guide tube housing at least one elongated member, a guide rack, and an anchor configured for disposal in a tubular tissue circumferentially offset from the guide rack. The anchor includes at least one guide tube attached to a suture having a first end and a second end. The at least one elongated member is deployed to puncture tubular tissue and mate with the at least one aperture of the anchor such that extraction of the at least one elongated member simultaneously draws out the suture through the punctured tubular tissue.

23 Claims, 8 Drawing Sheets

(56) References Cited

U.S. PATENT DOCUMENTS

| | | |
|---|---|---|
| 5,984,932 A | 11/1999 | Yoon |
| 5,993,466 A | 11/1999 | Yoon |
| 6,086,601 A | 7/2000 | Yoon |
| 6,206,893 B1 | 3/2001 | Klein et al. |
| 6,629,534 B1 | 10/2003 | St. Coar et al. |
| 6,997,931 B2 | 2/2006 | Sauer et al. |
| 2002/0198543 A1* | 12/2002 | Burdulis ............ A61B 17/0469 606/144 |
| 2004/0073238 A1 | 4/2004 | Makower |

* cited by examiner

METHODS AND DEVICES FOR TISSUE SUTURING

CROSS-REFERENCE TO RELATED APPLICATIONS

This application claims the benefit of and priority to U.S. Provisional Patent Application No. 62/057,394 filed Sep. 30, 2014 and U.S. Provisional Patent Application No. 62/057,387 filed Sep. 30, 2014, the entire disclosures of which are incorporated by reference herein.

BACKGROUND

The present disclosure relates to methods and devices for use in endoscopic surgery, in particular to methods and devices for suturing tissue to construct an anastomosis.

Technical Field

Numerous surgical procedures have been developed to replace veins and arteries that have become blocked by disease. As a result of aging and/or disease, veins and arteries may become blocked by plaque deposits, stenosis, or cholesterol. In some instances, these blockages can be treated with artherectomy, angioplasty or stent placement, and coronary bypass surgery is not required. Coronary bypass surgery may be required when these other methods of treatment cannot be used or have failed to clear the blocked vein or artery. In coronary bypass surgery, a vein is harvested from elsewhere in the body and grafted into place (i.e., between the aorta and the coronary artery) beyond the point of blockage by constructing an anastomosis.

Coronary bypass surgery requires a length of vein or artery for the graft. It is preferred to use a vein taken from the patient undergoing the bypass surgery, because they will not likely be rejected by the body after transplantation and grafting onto the aorta and coronary artery.

The left internal thoracic artery (LITA) is often harvested for coronary bypass surgery. However, the saphenous vein in the leg is also a good substitute for small veins or arteries such as the coronary arteries, and is often used in coronary bypass surgery. The cephalic vein in the arm is an alternative that is sometimes used.

Typically, sternotomy is utilized in coronary bypass surgery where harvesting and suturing is done by hand. However, sternotomy is a highly invasive procedure requiring extended recovery time.

Endoscopic procedures, such as thoracoscopy, enable a clinician to construct an anastomosis in an operation that requires only a few small incisions, and increases the patency of the vein. Endoscopic surgical techniques for operations such as gall bladder removal and hernia repair are now common. The surgeon performing the operation makes a few small incisions and inserts long tools, including forceps, scissors, and staplers into the incision and deep into the body. Viewing the tools through an endoscope, or a video display from an endoscope, the surgeon can perform all the cutting and suturing operations necessary for a wide variety of operations. The procedures are also referred to as endoscopic surgery, laparoscopic surgery, minimally invasive surgery, or video-assisted surgery. References to endoscopic surgery and endoscopes below is intended to encompass all of these fields, and all operations described below with reference to endoscopes can also be accomplished with laparoscopes, gastroscopes, and any other imaging devices which may be conveniently used.

Minimally invasive procedures for vein removal have been proposed. U.S. Pat. No. 5,373,840 shows a method of cutting the saphenous vein at one end, and grasping the vein with graspers or forceps, then sliding a ring over the vein while securing the vein at the same time.

SUMMARY

The present disclosure relates to a suturing device including a handle assembly, an elongated shaft extending from the handle assembly, and an end effector assembly disposed on a distal end of the elongated shaft. The handle assembly includes a trigger assembly. The end effector assembly includes at least one guide rod extending distally from the elongated shaft, at least one first guide tube extending distally from the elongated shaft, a guide rack disposed on the at least one guide rod, and an anchor disposed on a distal end of the at least one guide rod. The at least one first guide tube houses at least one elongated member. The guide rack includes at least one first aperture configured for locating the at least one guide rod and at least one second aperture configured for locating the at least one first guide tube. The anchor is circumferentially offset from the guide rack and is configured for disposal within tubular tissue. The anchor includes at least one aperture housing a second guide tube. The second guide tube is attached to a suture having a first end and a second end. A first actuation of the trigger assembly longitudinally extends the anchor into an incision in tubular tissue and longitudinally advances the guide rack such that tubular tissue is captured between the guide rack and the anchor. A second actuation of the trigger assembly deploys the at least one elongated member to puncture tubular tissue to mate with the at least one aperture of the anchor such that extraction of the at least one elongated member simultaneously draws out the first end of the suture through the punctured tubular tissue.

In disclosed aspects, the end effector assembly further includes a guide plate having a plurality of apertures configured for guiding the at least one guide rod and the at least one first guide tube.

In disclosed aspects, the at least one guide rod extends through the guide rack and operatively couples with the anchor.

In disclosed aspects, the anchor includes an atraumatic tip.

In disclosed aspects, the at least one elongated member is a flexible needle configured for puncturing tissue.

In disclosed aspects, mating the at least one elongated member with the at least one aperture of the anchor results in a press fit between the at least one elongated member and the at least one second guide tube of the anchor.

In disclosed aspects, further including a probe configured for locating the first end of the suture such that disposing the probe into a graft tubular tissue and passing the first end of the suture through a graft tubular tissue joins a graft tubular tissue with a tubular tissue.

The present disclosure also relates to a method of suturing tubular tissue. The method includes providing a suturing device for tubular tissue having a handle assembly, an elongated shaft extending from the handle assembly, and an end effector assembly disposed on a distal end of the elongated shaft. The end effector assembly includes at least one guide rod extending distally from the elongated shaft, at least one first guide tube extending distally from the elongated shaft, a guide rack disposed on the at least one guide rod, and an anchor disposed on a distal end of the at least one guide rod. The at least one first guide tube houses at least one elongated member. The guide rack includes at least one first aperture configured for locating the at least one guide rod and at least one second aperture configured for locating the at least one first guide tube. The anchor is circumferentially offset from the guide rack and is configured for disposal within tubular tissue. The anchor includes at least one aperture housing a second guide tube. The second guide tube is attached to a suture having a first end and a second end. The method also includes creating an incision in tubular tissue, extending the anchor into an incision in tubular tissue, advancing the guide rack such that tubular tissue is secured between the guide rack and the anchor, puncturing tubular tissue with the at least one elongated member, mating the at least one elongated member with the at least one aperture of the anchor, extracting the at least one elongated member, and extracting the suture through the punctured tubular tissue.

In disclosed aspects of the method, providing a suturing device includes a trigger assembly operatively coupled to the handle assembly and actuating the trigger assembly extends the anchor into an incision in tubular tissue.

In disclosed aspects of the method, further including securing tubular tissue between the anchor and the guide rack.

In disclosed aspects of the method, further including extending the at least one guide tube and seating the at least one guide tube into the at least one aperture of the guide rack.

In disclosed aspects of the method, further including translating the at least one elongated member through and along the at least one guide tube.

In disclosed aspects of the method, further including frictionally engaging the at least one elongated member with the second guide tube.

The present disclosure also related to an end effector for suturing tissue. The end effector includes an elongated shaft and an assembly attachable to an end of the elongated shaft. The assembly includes at least one guide rod extending distally from the elongated shaft, at least one first guide tube extending distally from the elongated shaft, and an anchor disposed on a distal end of the at least one guide rod. The at least one first guide tube houses at least one elongated member. The anchor is configured for being disposed within tubular tissue. The anchor includes at least one aperture housing a second guide tube. The second guide tube is attached to a suture having a first end and a second end. The anchor is extendable into an incision in tubular tissue. The at least one elongated member is deployable to puncture tubular tissue and mate with the at least one aperture of the anchor such that extraction of the at least one elongated member simultaneously draws out the first end of the suture through the punctured tubular tissue.

In disclosed aspects, the assembly includes a guide rack disposed on the guide rod, the guide rack having at least one first aperture configured for locating the at least one guide rod and at least one second aperture configured for locating the at least one first guide tube.

In disclosed aspects, the anchor is circumferentially offset from the guide rack.

In disclosed aspects, the guide rack is advanceable such that tubular tissue is captured between the guide rack and the anchor.

In disclosed aspects, the assembly further includes a guide plate having a plurality of apertures configured for guiding the at least one guide rod and the at least one first guide tube.

In disclosed aspects, the at least one guide rod extends through the guide rack and operatively couples with the anchor.

In disclosed aspects, mating the at least one elongated member with the at least one aperture of the anchor results in a press fit between the at least one elongated member and the at least one second guide tube of the anchor.

In disclosed aspects, further includes a probe configured for locating the first end of the suture such that disposing the probe into a graft tubular tissue and passing the first end of the suture through a graft tubular tissue joins a graft tubular tissue with a tubular tissue.

BRIEF DESCRIPTION OF THE DRAWINGS

Various embodiments of the surgical devices are described herein with reference to the drawings wherein.

DETAILED DESCRIPTION

Figure 1:
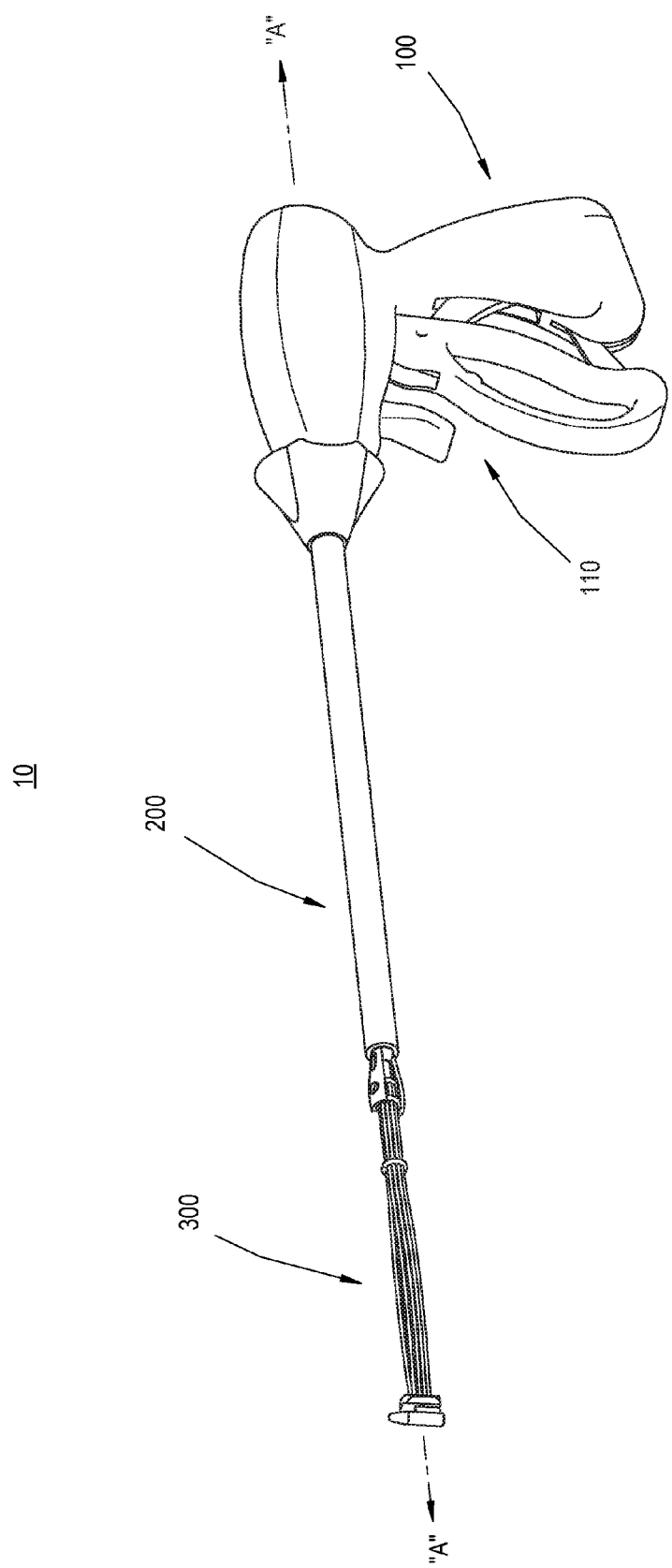
FIG. 1 illustrates a suturing device for tubular tissue in accordance with one embodiment of the present disclosure.

Embodiments of the presently disclosed suturing device are described in detail with reference to the drawings, in which like reference numerals designate identical or corresponding elements in each of the several views. As used herein the term "distal" refers to that portion of the device that is farther from the user, while the term "proximal" refers to that portion of the device that is closer to the user.

Figure 2B:
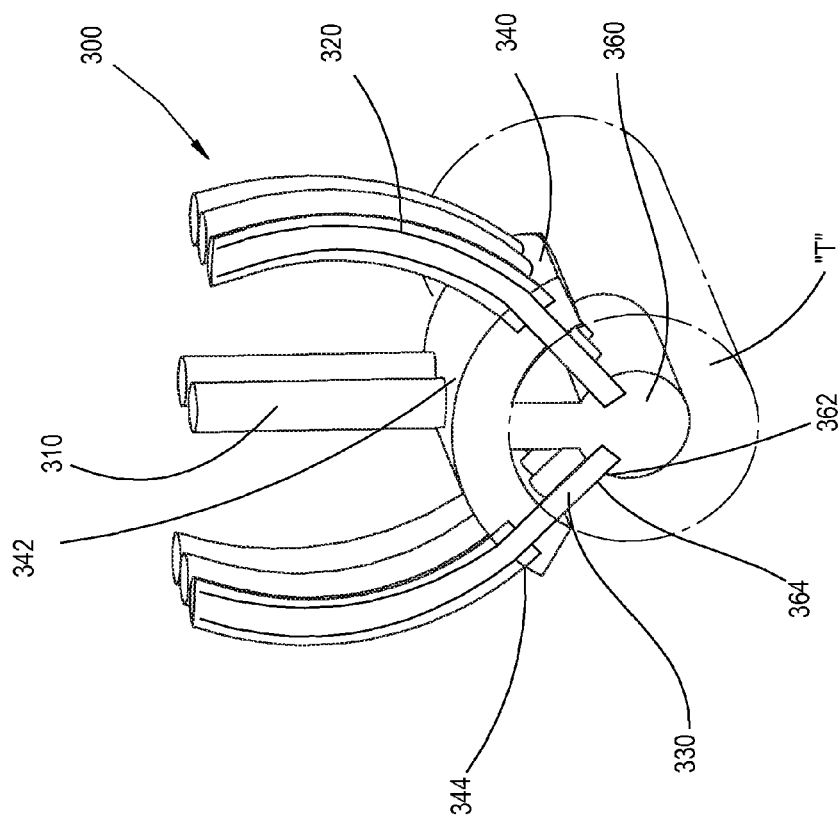
FIGS. 2A and 2B are perspective views of a distal end of the suturing device of FIG. 1 shown in engagement with tubular tissue.
Figure 2A:
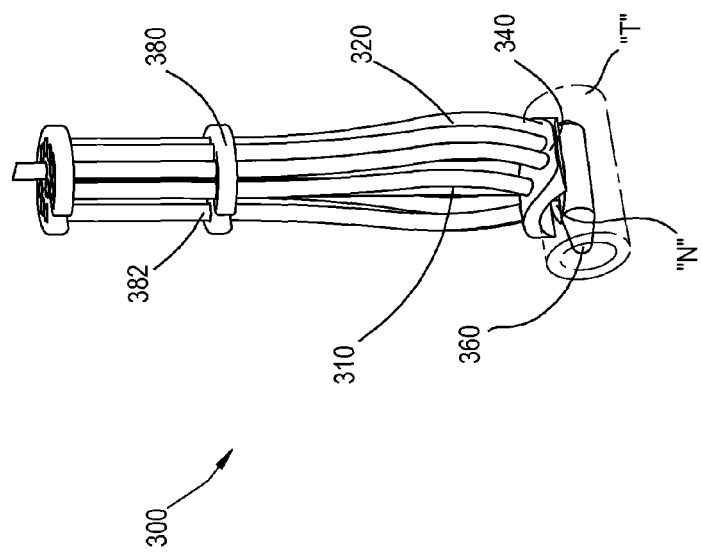
Figure 3:
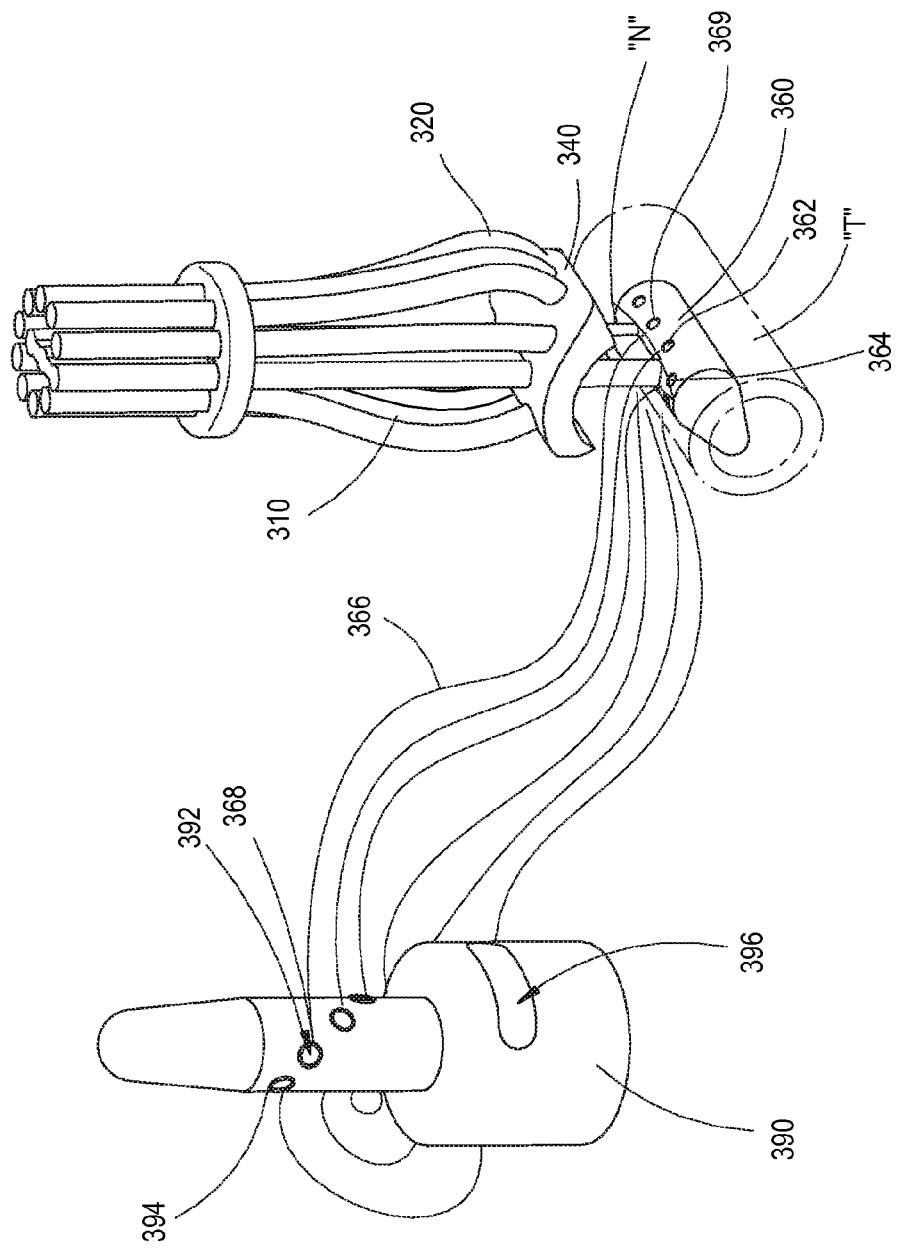
FIG. 3 is a perspective view of a distal end of the suturing device of FIGS. 1 and 2 shown in engagement with tubular tissue having sutures extracted therefrom.

Referring initially to FIGS. 1-3, one embodiment of a suturing device 10 is shown for use with various surgical procedures and generally includes a handle assembly 100, an elongated shaft 200 extending distally from handle assembly 100 and defining a longitudinal axis "A-A." An end effector assembly 300 is disposed on a distal end of the elongated shaft 200.

As shown in FIGS. 2A and 2B, in one embodiment, end effector assembly 300 includes a plurality of guide rods 310, a plurality of guide tubes 320, a plurality of elongated members 330 disposed within guide tubes 320, a guide rack 340 disposed on guide rods 310, an anchor 360, and a guide plate 380.

Guide rods 310 are configured to provide structure and support for the components of end effector assembly 300 as the components translate in response to actuation of a trigger assembly 110 of handle assembly 100. Though the embodiment in FIG. 2A shows three guide rods 310, it is contemplated that end effector assembly 300 would properly function with a greater or lesser number of guide rods 310. In one embodiment, guide rods 310 are stainless steel rods. However, it is contemplated that any appropriate biocompatible material may be used. In one embodiment, end effector assembly also includes a guide plate 380. Guide plate 380 includes a plurality of apertures 382 configured to direct the guide tubes 320 toward guide rack 340.

Continuing with FIGS. 2A and 2B, guide rack 340 is slidably disposed on guide rods 310 and is movable along guide rods 310 to secure tubular tissue "T" between anchor 360 and guide rack 340 such that movement of tubular tissue "T" is limited during the use of suturing device 10. Guide rack 340 defines a plurality of guide rod apertures 342. Guide rod apertures 342 are correspondingly sized for guide rods 310 such that the plurality of guide rods 310 are able to pass through the plurality of guide rod apertures 342.

Guide rack 340 also defines a plurality of guide tube apertures 344. Guide tube apertures 344 are correspondingly sized for guide tubes 320. As shown in FIG. 2B, in one embodiment, guide tube apertures 344 are sized to seat guide tubes 320 while elongated members 330 extend entirely through guide rack 340. For example, in one embodiment, guide tubes 320 are approximately 23 AWG polyimide guide tubes. In this embodiment, guide tube apertures 344 are correspondingly sized such that guide tubes 320 extend only partially through guide rack 340. Though the embodiments in FIGS. 2A, 2B, and 3 depicts end effector assembly 300 to include eight guide tubes 320, it is contemplated that any appropriate number of guide tubes 320 may be used (i.e., more or less than 8 guide tubes 320).

In one embodiment, as shown in FIG. 2B, elongated members 330 are flexible nitinol rods including a sharp tip (not shown). The flexibility of guide tubes 320 and elongated members 330 enables suturing device 10 to be used in a wide variety of configurations.

Elongated members 330 extend through guide rack 340 to puncture tubular tissue "T" and mate with a plurality of anchor apertures 362 formed on anchor 360. As shown in FIG. 2B, each anchor aperture 362 houses a suture guide tube portion 364. In one embodiment, suture guide tube portions 364 are approximately 80 AWG polyimide tubes. Suture guide tube portions 364 are sized such that insertion of the elongated members 330 into the suture guide tube portions 364 creates a press fit between the two components.

Suture guide tube portions 364 are each attached to a suture 366. As a result of the press fit between elongated members 330 and suture guide tube portions 364, extracting elongated members 330 also draws out a plurality of first ends 368 of sutures 366 through punctured tubular tissue "T." This inside-out technique of suturing tubular tissue "T" maximizes intimal contact between tubular tissue "T" and a graft tubular tissue "GT" (FIG. 6) thereby increasing the likelihood of anastomotic patency relative to methods which do not provide such intimal contact.

As shown in FIG. 3, first ends 368 of sutures 366 are drawn out through the punctured tubular tissue "T" and located on a probe 390. Similar to anchor 360, probe 390 includes a plurality of probe apertures 392. Probe apertures 392 are configured for seating first ends 368 of sutures 366. As a result, first ends 368 of sutures 366 are located in probe 390 while second ends 369 of sutures 366 remain located in anchor 360.

As will be detailed below with reference to FIGS. 3-5, probe 390 is configured to mate with a suturing device 20. Suturing device 20 is configured for retrieving the first ends 368 of sutures 366 from the inside of graft tubular tissue "GT."

Figure 4:
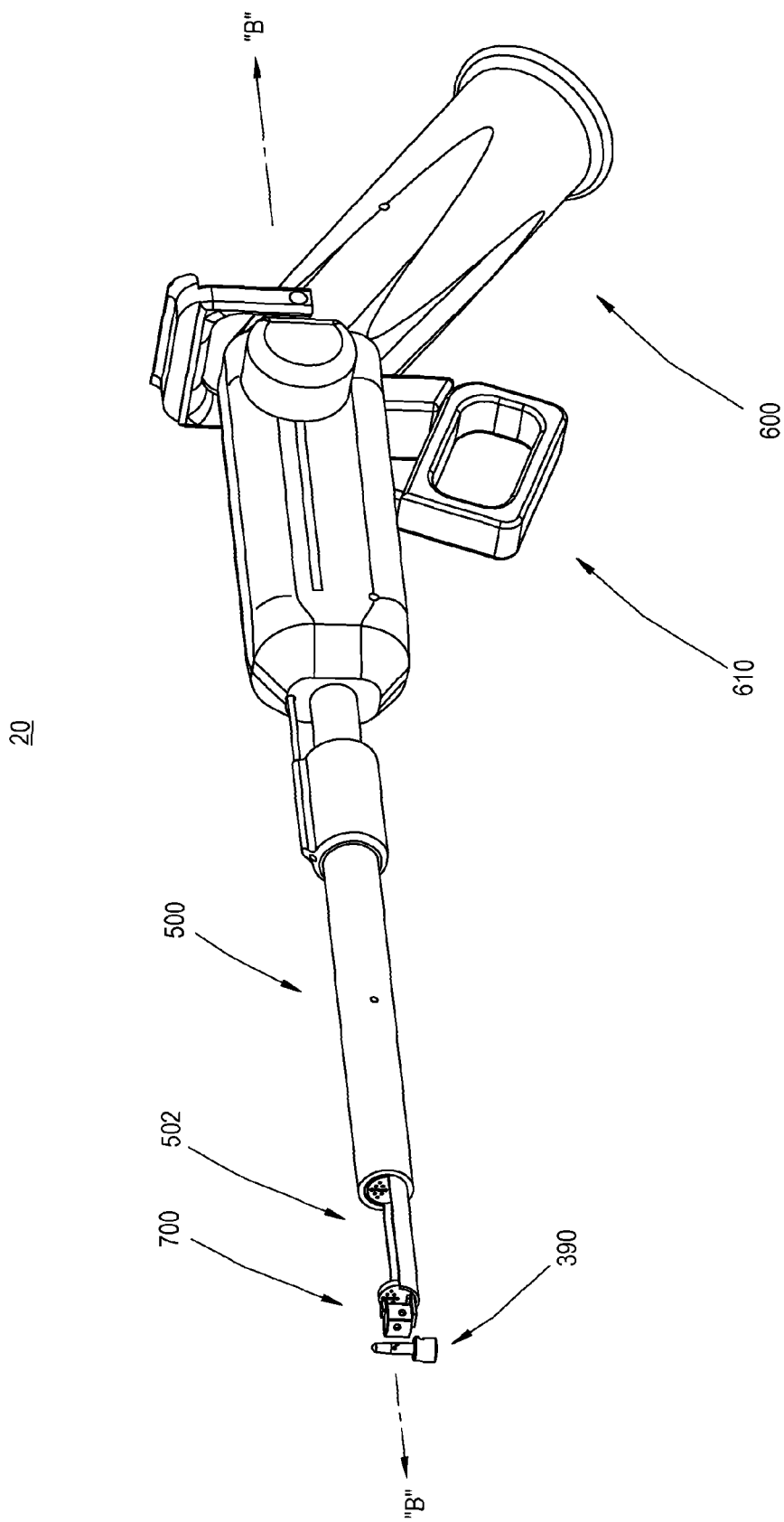
FIG. 4 illustrates a suturing device for tubular tissue in accordance with an embodiment of the present disclosure.

One embodiment of suturing device 20 is shown in FIG. 4 for use with various surgical procedures and generally includes a handle assembly 600, an elongated shaft 500 extending distally from handle assembly 600 and defining a longitudinal axis "B-B." An end effector assembly 700 is disposed on a distal portion 502 of the elongated shaft 500.

Figure 5A:
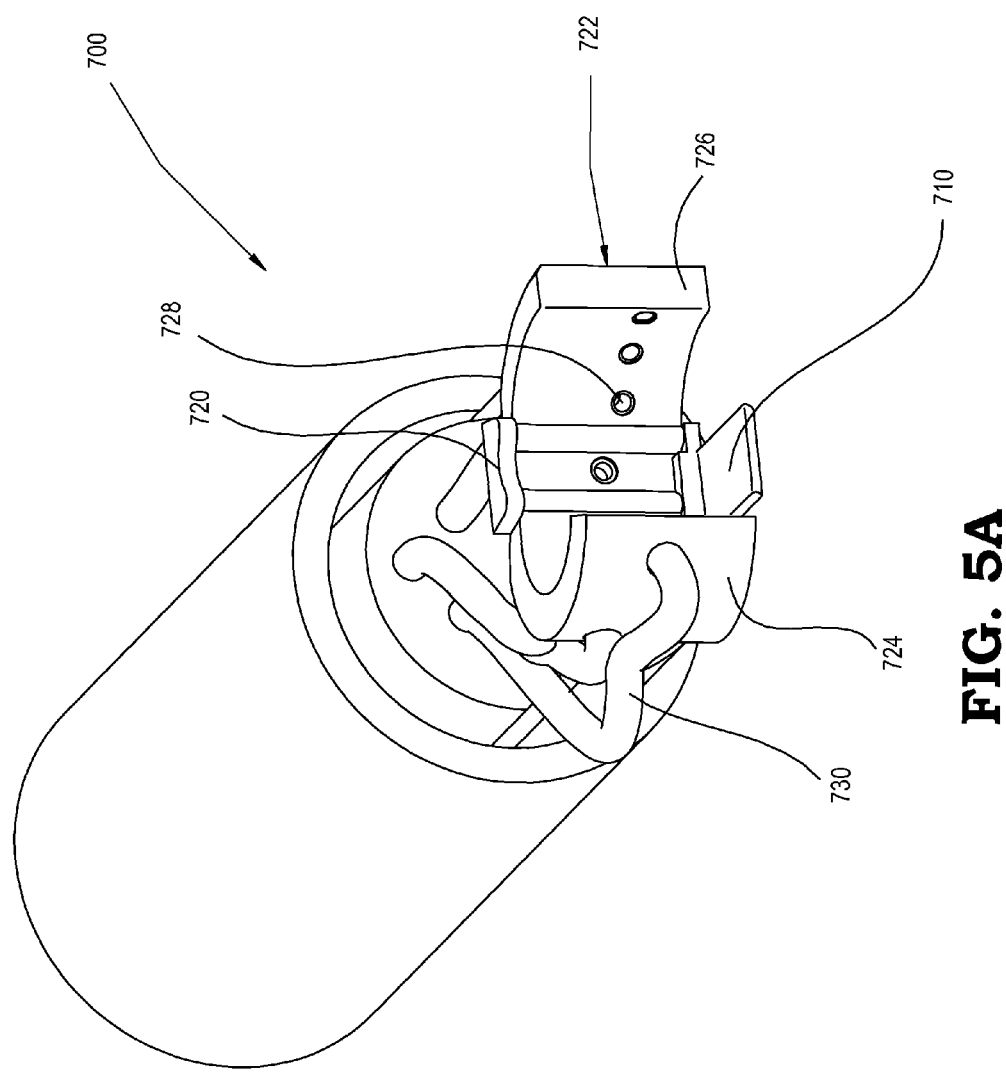
FIG. 5A illustrates a perspective view of a distal end of the suturing device of FIG. 4 in the open position.
Figure 5B:
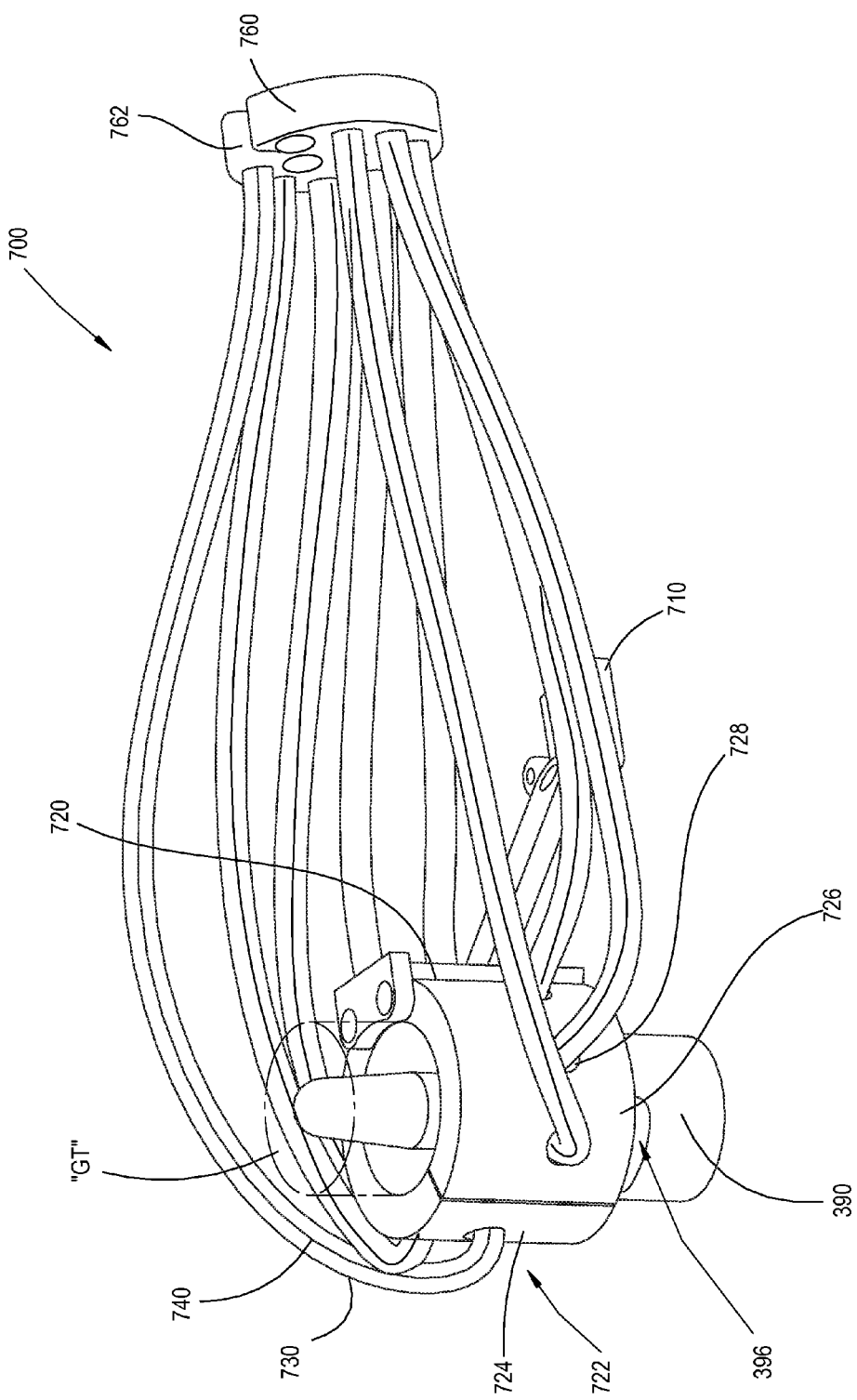
FIG. 5B illustrates a perspective view of a distal end of the suturing device of FIG. 4 in the approximated position.

An embodiment of end effector assembly 700 is shown in FIGS. 5A and 5B. End effector assembly includes a mating plate 710 extending distally from elongated shaft 500 (FIG. 4). Mating plate 710 is a rigid structure configured for supporting a hinge 720. Hinge 720 is operatively coupled to a clamshell 722. Clamshell 722 includes a first clamshell half 724 and a second clamshell half 726 and is configured for opening and approximating first and second clamshell halves 724 and 726. For example, in FIG. 5A, first and second clamshell halves 724 and 726 are shown in the spaced apart position and in FIG. 5B, first and second clamshells halves 724 and 726 are shown approximated around a graft tubular tissue "GT." In one embodiment as shown in FIG. 5B, end effector assembly 700 also includes a guide plate 760 defining a plurality of apertures 762 configured to direct the guide tubes 730 toward clamshell 722.

Similar to guide rack 340, first and second clamshell halves 724 and 726 define a plurality of clamshell apertures 728 configured for locating a plurality of guide tubes 730 extending from elongated shaft 500 and a plurality of elongated members 740 (FIG. 5B) extending from elongated shaft 500 and disposed within guide tubes 730. In one embodiment, guide tubes 730 are polyimide guide tubes similar to guide tubes 320 of suturing device 10. In one embodiment, elongated members 740 are flexible nitinol rods including a sharp tip (not shown). The flexibility of guide tubes 730 and elongated members 740 enables suturing device 20 to be used in a wide variety of configurations. Guide tubes 730 are configured to sit into clamshell apertures 728 to direct elongated members 740 into clamshell apertures 728. It is contemplated that subsequent to locating the guide tubes 730 using the clamshell apertures 728, guide tubes 730 may be secured in position by welding, an adhesive, or another suitable arrangement for joining. It is also contemplated that the guide tubes 730 may bend upon extension to increase the radius that the elongated members 740 travel within the respective guide tubes 730, thereby effectively reducing friction inside the guide tubes 730 between the elongated members 740 and inner walls of guide tubes 730.

As noted above, probe 390 is configured to mate with suturing device 20 to retrieve sutures 366 from within graft tubular tissue "GT." In order to achieve radial alignment between the probe apertures 392 and the clamshell apertures 728, probe 390 defines a slot 396 (FIGS. 3 and 5B) extending therethrough and configured for coupling with mating plate 710. In one embodiment, as shown in FIG. 5B, slot 396 and mating plate 710 are configured to mate via a male-female mechanism and are sized accordingly. Approximating first and second clamshell halves 724 and 726 around graft tubular tissue "GT" and mating with probe 390 compressibly secures tubular graft tissue "GT."

Figure 6:
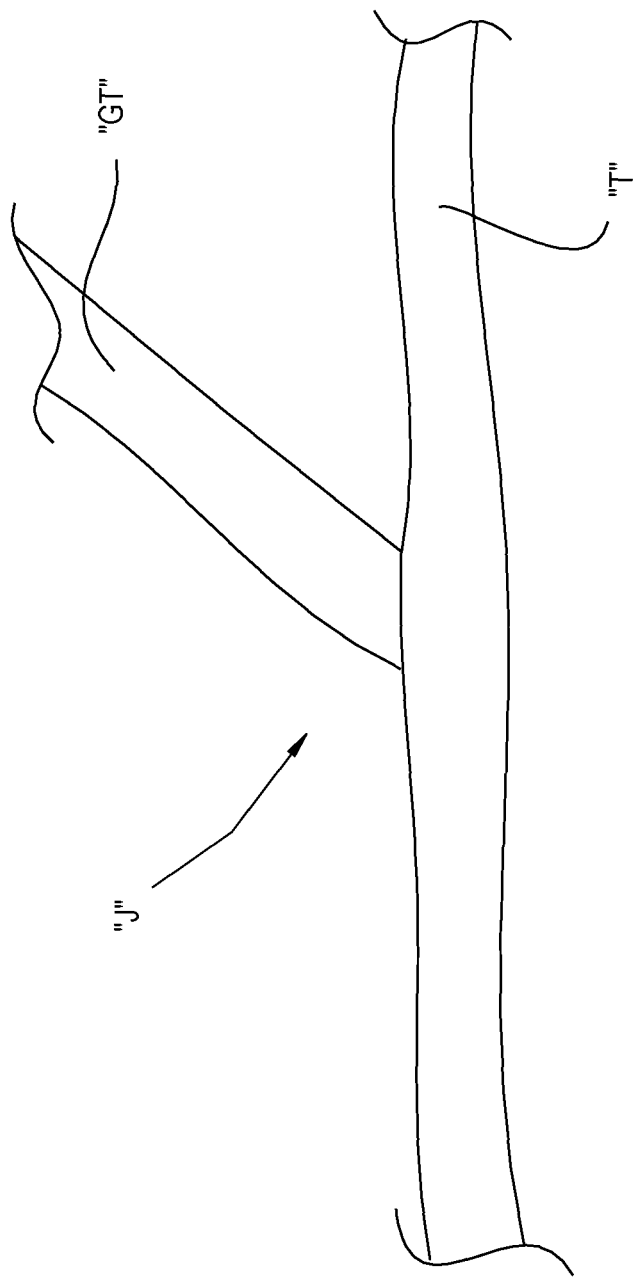
FIG. 6 is a side view of a junction between tubular tissue and graft tubular tissue.

Elongated members 740 are extendable through clamshell apertures 728 and to puncture graft tubular tissue "GT" to extract first ends 368 of sutures 366 from inside tubular graft tissue "GT." Referring to FIG. 3, the extraction of sutures 366 from inside graft tubular tissue "GT" utilizes a similar process to that of the extraction of sutures 366 from inside tubular tissue "T." Each probe aperture 392 houses a suture guide tube portion 394. Suture guide tube portions 394 are sized such that insertion of elongated members 740 into the suture guide tube portions 394 creates a press fit between the two components. Each suture guide tube portion 394 is attached to a suture 366. As a result of the press fit between elongated members 740 and suture guide tube portions 364, extraction of elongated members 740 from probe 390 draws out sutures 366 through punctured tubular graft tissue "GT." As shown in FIG. 6, this operation creates a junction between tubular tissue "T" and graft tubular tissue "GT."

Figure 7:
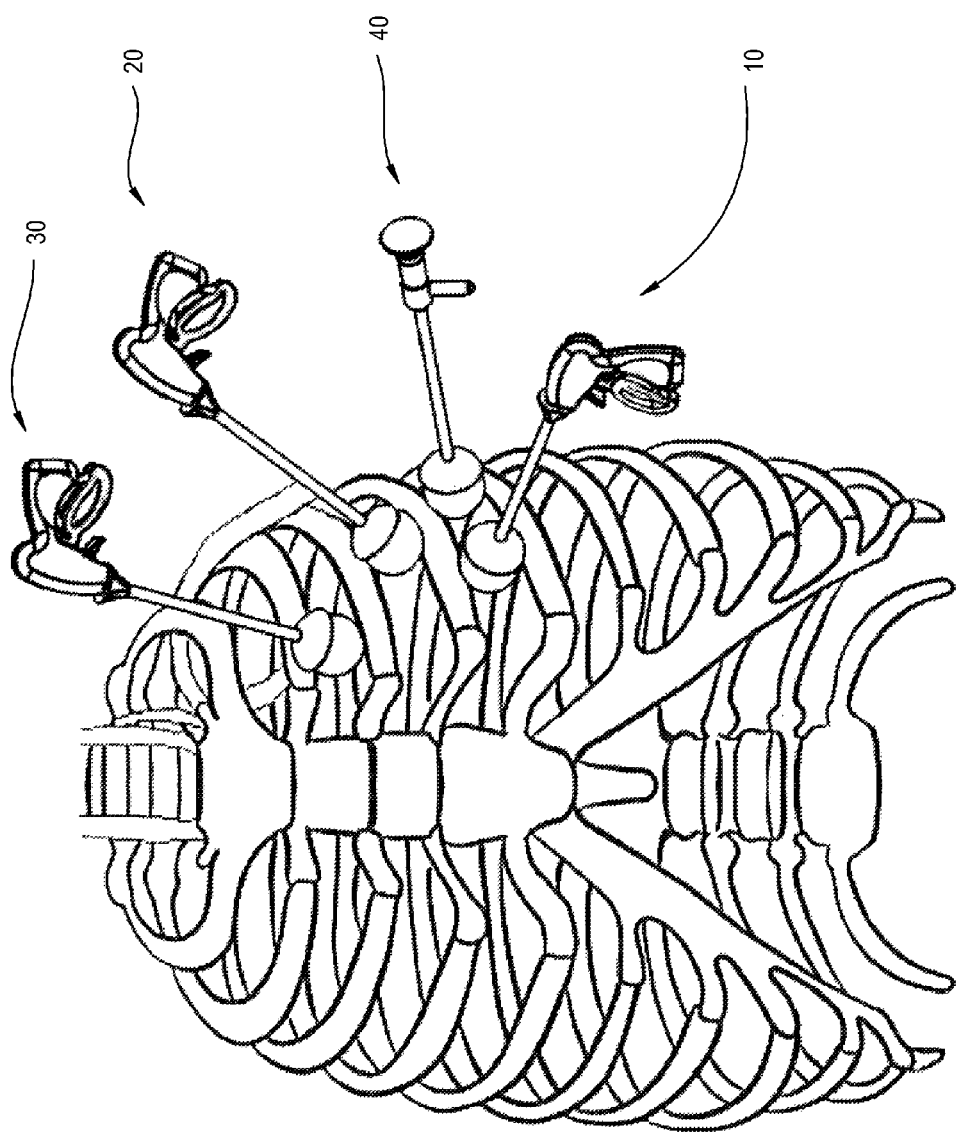
FIG. 7 illustrates suturing devices with their distal ends inserted through access devices and positioned in a thoracic cavity of a patient in accordance with embodiments of the present disclosure.

With additional reference to FIG. 7, in operation, an endoscope 40 is used to locate the target tubular tissue "T." Once located, an incision "N" is made in target tubular tissue "T" as shown in FIG. 2A. In one embodiment, incision "N" is approximately 2-3 mm. Upon actuation of trigger assembly 110, anchor 360 of suturing device 10 is extended from guide rack 340 into incision "N" of tubular tissue "T." Guide rack 340 is then translated along guide rods 310 towards anchor 360 to secure tubular tissue "T" between guide rack 340 and anchor 360. Once tubular tissue "T" is secured, elongated members 330 are deployed through guide tubes 320 and travel along guide tubes 320 into guide rack apertures 344. While guide tubes 320 sit on guide rack apertures 344, elongated members 330 extend through guide rack apertures 344 to puncture tubular tissue "T" and mate with suture guide tube portions 364. Due to the press fit between suture guide tube portions 364 and elongated members 330, extracting elongated members 330 out of anchor 360 simultaneously draws out the suture guide tube portions 364 and the sutures 366 attached therewith. Once first ends 368 of sutures 366 are outside of tubular tissue "T," guide rack 340 is translated away from anchor 360 and anchor 360 is withdrawn from inside tubular tissue "T" through incision "N." As a result of this first procedure, a circular pattern is created by sutures 366 around incision "N" of tubular tissue "T." However, in some embodiments, sutures 366 may also create an elliptical, oval, or any other suitable pattern.

In preparation for the second procedure, first ends 368 of sutures 366 are seated into probe apertures 392 as shown in FIG. 3. Probe 390 is disposed in an open end of tubular graft tissue to mate with suturing device 20. As shown in FIG. 7, suturing device 20 is inserted into the surgical field near the location of tubular graft tissue "GT." Trigger assembly 610 of suturing device 20 is first actuated to open first and second clamshell halves 724 and 726 and actuated again to approximate first and second clamshell halves 724 and 726 concentrically around graft tubular tissue "GT" and probe 390. Concomitantly, mating plate 710 couples with slot 396 in a male-female mechanism (FIG. 5B). Once graft tubular tissue "GT" is secured between probe 390 and approximated first and second clamshell halves 724 and 726, elongated members 740 are deployed. Elongated members 740 extend through and along guide tubes 730 into clamshell apertures 728. While guide tubes 730 sit on clamshell apertures 728, elongated members 740 extend through and into clamshell apertures 728 to puncture tubular graft tissue "GT." Inside tubular graft tissue "GT," elongated members 740 mate with suture guide tube portions 394. Due to the press fit between suture guide tube portions 394 and elongated members 740, extracting the elongated members 740 from within tubular graft tissue "GT," simultaneously draws out the suture guide tube portions 394 and the sutures 366 attached therewith. When first ends 368 of sutures 366 are outside of tubular graft tissue "GT," first and second clamshell halves 724 and 726 are opened and probe 390 is withdrawn from inside tubular graft tissue "GT." At the completion of the second procedure, a junction "J" (FIG. 6) is formed between tubular tissue "T" and tubular graft tissue "GT." A suture tying device 30 is then inserted into the surgical field to tie sutures 366 to complete the construction of the anastomosis.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of various embodiments. Those skilled in the art will envision other modifications within the scope and spirit of the claims appended hereto.

What is claimed is:

1. A suturing device for tubular tissue, comprising:
   a handle assembly including a trigger assembly;
   an elongated shaft extending from the handle assembly; and
   an end effector assembly disposed on a distal end of the elongated shaft, the end effector assembly including:
   at least one guide rod extending distally from the elongated shaft;
   at least one first guide tube extending distally from the elongated shaft, the at least one first guide tube housing at least one elongated member;
   a guide rack disposed on the guide rod, the guide rack having at least one first aperture configured for locating the at least one guide rod and at least one second aperture configured for locating the at least one first guide tube; and
   an anchor disposed on a distal end of the at least one guide rod, the anchor being circumferentially offset from the guide rack and being configured for disposal within tubular tissue, the anchor having:
   at least one aperture housing a second guide tube, the second guide tube attached to a suture having a first end and a second end; wherein a first actuation of the trigger assembly longitudinally extends the anchor into an incision in tubular tissue and longitudinally advances the guide rack such that tubular tissue is captured between the guide rack and the anchor and a second actuation of the trigger assembly deploys the at least one elongated member to puncture tubular tissue and mate with the at least one aperture of the anchor such that extraction of the at least one elongated member simultaneously draws out the first end of the suture through the punctured tubular tissue.

2. The suturing device according to claim 1, wherein the end effector assembly further includes a guide plate having a plurality of apertures configured for guiding the at least one guide rod and the at least one first guide tube.

3. The suturing device according to claim 1, wherein the at least one guide rod extends through the guide rack and operatively couples with the anchor.

4. The suturing device according to claim 1, wherein the anchor includes an atraumatic tip.

5. The suturing device according to claim 1, wherein the at least one elongated member is a flexible needle configured for puncturing tissue.

6. The suturing device according to claim 1, wherein mating the at least one elongated member with the at least one aperture of the anchor results in a press fit between the at least one elongated member and the at least one second guide tube of the anchor.

7. The suturing device according to claim 1, further including a probe configured for locating the first end of the suture such that disposing the probe into a graft tubular tissue and passing the first end of the suture through a graft tubular tissue joins a graft tubular tissue with a tubular tissue.

8. A method of suturing tubular tissue, the method comprising:
providing a suturing device for tubular tissue, the suturing device including:
a handle assembly:
an elongated shaft extending from the handle assembly;
an end effector assembly disposed on a distal end of the elongated shaft, the end effector assembly having:
at least one guide rod extending distally from the elongated shaft;
at least one first guide tube extending distally from the elongated shaft, the at least one first guide tube housing at least one elongated member;
a guide rack disposed on the guide rod, the guide rack having at least one first aperture configured for locating the at least one guide rod and at least one second aperture configured for locating the at least one first guide tube; and
an anchor disposed on a distal end of the at least one guide rod, the anchor being circumferentially offset from the guide rack and being configured for disposal within tubular tissue, the anchor having:
at least one aperture including a second guide tube, the second guide tube attached to a suture having a first end and a second end;
creating an incision in tubular tissue;
extending the anchor into an incision in tubular tissue;
advancing the guide rack such that tubular tissue is secured between the guide rack and the anchor;
puncturing tubular tissue with the at least one elongated member;
mating the at least one elongated member with the at least on aperture of the anchor;
extracting the at least one elongated member; and
extracting the suture through the punctured tubular tissue.

9. The method according to claim 8, wherein providing a suturing device includes a trigger assembly coupled to a handle assembly and actuating the trigger assembly extends the anchor into an incision in tubular tissue.

10. The method according to claim 8, further comprising:
securing tubular tissue between the anchor and the guide rack.

11. The method according to claim 8, further comprising:
extending the at least one guide tube; and
seating the at least one guide tube into the at least one second aperture of the guide rack.

12. The method according to claim 8, further comprising:
translating the at least one elongated member through and along the at least one guide tube.

13. The method according to claim 8, further comprising:
frictionally engaging the at least one elongated member with the second guide tube.

14. An end effector for suturing tissue comprising:
an elongated shaft; and
an assembly attachable to an end of the elongated shaft, the assembly including:
at least one guide rod extending distally from the elongated shaft;
at least one first guide tube extending distally from the elongated shaft, the at least one first guide tube housing at least one elongated member;
an anchor disposed on a distal end of the at least one guide rod, the anchor being configured for disposal within tubular tissue, the anchor having:
at least one aperture housing a second guide tube, the second guide tube attached to a suture having a first end and a second end; wherein the anchor is extendable into an incision in tubular tissue and the at least one elongated member is deployable to puncture tubular tissue and mate with the at least one aperture of the anchor such that extraction of the at least one elongated member simultaneously draws out the first end of the suture through the punctured tubular tissue.

15. The end effector according to claim 14, wherein the assembly includes a guide rack disposed on the guide rod, the guide rack having at least one first aperture configured for locating the at least one guide rod and at least one second aperture configured for locating the at least one first guide tube.

16. The end effector according to claim 15, wherein the anchor is circumferentially offset from the guide rack.

17. The end effector according to claim 15, wherein the guide rack is advanceable such that tubular tissue is captured between the guide rack and the anchor.

18. The end effector according to claim 14, wherein the assembly further includes a guide plate having a plurality of apertures configured for guiding the at least one guide rod and the at least one first guide tube.

19. The end effector according to claim 15, wherein the at least one guide rod extends through the guide rack and operatively couples with the anchor.

20. The end effector according to claim 14, wherein the anchor includes an atraumatic tip.

21. The end effector according to claim 14, wherein the at least one elongated member is a flexible needle configured for puncturing tissue.

22. The end effector according to claim 14, wherein mating the at least one elongated member with the at least one aperture of the anchor results in a press fit between the at least one elongated member and the at least one second guide tube of the anchor.

23. The end effector according to claim 14, further including a probe configured for locating the first end of the suture such that disposing the probe into a graft tubular tissue and passing the first end of the suture through a graft tubular tissue joins a graft tubular tissue with a tubular tissue.

* * * * *